United States Patent
Mahler et al.

(10) Patent No.: US 10,638,794 B2
(45) Date of Patent: May 5, 2020

(54) EXTENDED HEATER AND HEATING ASSEMBLY FOR AN AEROSOL GENERATING SYSTEM

(71) Applicant: Philip Morris Products S.A., Neuchatel (CH)

(72) Inventors: Boris Mahler, Chamblon (CH); Mirko Minzoni, Neuchatel (CH); Julien Plojoux, Geneva (CH)

(73) Assignee: Philip Morris Products S.A., Neuchatel (CH)

( * ) Notice: Subject to any disclaimer, the term of this patent is extended or adjusted under 35 U.S.C. 154(b) by 135 days.

(21) Appl. No.: 15/553,216

(22) PCT Filed: Mar. 22, 2016

(86) PCT No.: PCT/EP2016/056223
§ 371 (c)(1),
(2) Date: Aug. 24, 2017

(87) PCT Pub. No.: WO2016/156103
PCT Pub. Date: Oct. 6, 2016

(65) Prior Publication Data
US 2018/0235278 A1    Aug. 23, 2018

(30) Foreign Application Priority Data

Mar. 31, 2015    (EP) .................................... 15162071

(51) Int. Cl.
*A24F 47/00* (2020.01)
*F22B 1/28* (2006.01)
*A61M 11/04* (2006.01)

(52) U.S. Cl.
CPC ............ *A24F 47/008* (2013.01); *F22B 1/284* (2013.01); *A61M 11/042* (2014.02)

(58) Field of Classification Search
None
See application file for complete search history.

(56) References Cited

U.S. PATENT DOCUMENTS

| 3,964,943 A | 6/1976 | Andersen |
|---|---|---|
| 4,241,292 A | 12/1980 | Kreick |
| (Continued) | | |

FOREIGN PATENT DOCUMENTS

| CN | 102595943 A | 7/2012 |
|---|---|---|
| CN | 103987286 A | 8/2014 |
| (Continued) | | |

OTHER PUBLICATIONS

International Search Report and Written Opinion dated Jun. 28, 2016 in PCT/EP2016/056223, filed Mar. 22, 2016.
(Continued)

*Primary Examiner* — Dennis R Cordray
(74) *Attorney, Agent, or Firm* — Oblon, McClelland, Maier & Neustadt, L.L.P.

(57) ABSTRACT

A heating assembly for heating an aerosol-forming substrate is provided, including a heater including an electrically resistive heating element and a heater substrate; and a heater mount coupled to the heater, the heating element including a first portion and a second portion configured such that, when an electrical current is passed through the heating element, the first portion is heated to a higher temperature than that of the second portion, the first portion of the heating element being disposed on a heating area of the heater substrate and the second portion of the heating element being disposed on a holding area of the heater substrate, the heater mount being fixed to the holding area of the heater substrate, and the second portion of the heating element being longer than the first portion of the heating element.

13 Claims, 4 Drawing Sheets

(56) References Cited

U.S. PATENT DOCUMENTS

| | | | |
|---|---|---|---|
| 5,530,225 A * | 6/1996 | Hajaligol | A24F 47/008 |
| | | | 131/194 |
| 9,674,894 B2 * | 6/2017 | Schneider | A24F 47/008 |
| 2005/0172976 A1 | 8/2005 | Newman et al. | |
| 2011/0155151 A1 | 6/2011 | Newman et al. | |
| 2011/0155718 A1 | 6/2011 | Greim | |
| 2011/0290269 A1 | 12/2011 | Shimizu | |
| 2012/0260927 A1 | 10/2012 | Liu | |
| 2014/0064715 A1 | 3/2014 | Greim et al. | |
| 2014/0305449 A1 * | 10/2014 | Plojoux | A24F 47/008 |
| | | | 131/328 |
| 2014/0345634 A1 * | 11/2014 | Zuber | A24F 47/004 |
| | | | 131/329 |
| 2014/0373856 A1 | 12/2014 | Zuber et al. | |
| 2015/0163859 A1 | 6/2015 | Schneider et al. | |

FOREIGN PATENT DOCUMENTS

| | | |
|---|---|---|
| EA | 012883 B1 | 12/2009 |
| EP | 1600066 A2 | 11/2005 |
| EP | 2 110 033 A1 | 10/2009 |
| EP | 2 316 286 A1 | 5/2011 |
| EP | 2 340 730 | 7/2011 |
| EP | 2 394 520 | 12/2011 |
| EP | 1993388 B1 | 8/2012 |
| GB | 2 473 264 | 3/2011 |
| KR | 10-0636287 | 10/2006 |
| RU | 76781 U1 | 10/2008 |
| UA | 41898 C2 | 10/2001 |
| WO | WO 2011/050964 A1 | 5/2011 |
| WO | WO 2011/063970 | 6/2011 |
| WO | WO 2012/065310 | 5/2012 |
| WO | WO 2013/098409 A1 | 7/2013 |
| WO | WO 2013/098410 A2 | 7/2013 |
| WO | WO 2014/102092 A1 | 7/2014 |
| WO | WO 2015/082653 A1 | 6/2015 |

OTHER PUBLICATIONS

Extended European Search Report dated Aug. 20, 2015 in Patent Application No. 15162071.3.
Office Action dated Jul. 22, 2015 in Japanese Patent Application No. 2015-522126 (submitting English translation only).
Written Opinion of the International Search Authority dated May 14, 2014 in PCT/EP13/076970 Filed Dec. 17, 2013.
International Search Report dated May 14, 2014 in PCT/EP13/076970 Filed Dec. 17, 2013.
Korean Office Action (English translation) dated Apr. 23, 2016 in Korean Application No. 10-2015-7022087 (3 pages).
Translation of Decision to Grant dated Sep. 15, 2016 in Russian application No. 2015131116 (5 pages).
Korean Office Action (English translation only) dated Feb. 1, 2017 in Korean divisional application No. 10-2016-7026500, citing document AU therein (6 pages).
Russian Notice of Allowance with English translation dated Aug. 28, 2019 in Russian Patent Application No. 2017134602, citing document AO therein (16 pages).
Chinese Office Action with English translation dated Dec. 19, 2019 in corresponding Chinese Patent Application No. 201680015386.0, citing documents AO and AP therein (18 pages).

* cited by examiner

EXTENDED HEATER AND HEATING ASSEMBLY FOR AN AEROSOL GENERATING SYSTEM

The specification relates to a heating assembly suitable for use in an aerosol-generating device or aerosol-generating system. In particular the invention relates to a heating assembly having an extended heater suitable for insertion into an aerosol-forming substrate of a smoking article in order to internally heat the aerosol-forming substrate.

There is increasing demand for handheld aerosol-generating devices that are able to deliver aerosol for user inhalation. One particular area of demand is for heated smoking devices in which an aerosol-forming substrate is heated to release volatile flavour compounds, without combustion of the aerosol-forming substrate. The released volatile compounds are conveyed within an aerosol to the user.

Any aerosol-generating device that operates by heating an aerosol-forming substrate must include a heating assembly. A number of different types of heating assembly have been proposed for different types of aerosol-forming substrate.

One type of heating assembly that has been proposed for heated smoking devices operates by inserting a heater into a solid aerosol-forming substrate, such as a plug of tobacco. This arrangement allows the substrate to be heated directly and efficiently. But there are number of technical challenges with this type of heating assembly, including meeting requirements for small size, robustness, low manufacturing cost, sufficient operating temperatures and effective localisation of generated heat.

Heated aerosol-generating articles comprising tobacco for generation of an aerosol by heating rather than burning are known in the art. Tobacco used as part of an aerosol-forming substrate in heated aerosol-generating articles is designed to produce an aerosol when heated rather than when burned. Thus, such tobacco typically contains high levels of aerosol formers, such as glycerine or propylene glycol. If a user were to light a heated aerosol-generating article and smoke it as if it were a conventional cigarette that user would not receive the intended user experience. It would be desirable to produce a heated aerosol-generating article that has a lowered propensity for flame ignition. Such a heated aerosol-generating article would be preferably difficult to light during attempts to light the article with a lighter, such as a flame, in the manner of traditional cigarettes. One way to form a heated aerosol-generating article that has a lowered propensity for flame ignition may be to arrange a tube at a distal end of the article to protect the aerosol-forming substrate from direct contact with a flame.

It would be desirable to provide a robust, inexpensive heating assembly for an aerosol-generating device that provides a localised source of heat for heating an aerosol-forming substrate. It would be desirable to provide a heating assembly that is more suitable for use with an aerosol-generating article having a non-consumable element located at a distal end of the article, for example a hollow tube.

In a first aspect of the invention, there is provided a heating assembly for heating an aerosol-forming substrate, the heating assembly comprising: a heater comprising an electrically resistive heating element and a heater substrate; and a heater mount coupled to the heater; wherein the electrically resistive heating element comprises a first portion and a second portion configured such that, when an electrical current is passed through the heating element the first portion is heated to a higher temperature than the second portion, wherein the first portion of the heating element is positioned on a heating area of the heater substrate and the second portion of the heating element is positioned on a holding area of the heater substrate; wherein the heater mount is fixed to the holding area of the heater substrate, and wherein the second portion of the electrically resistive heating element is longer than the first portion of the heating element. That is, the second portion extends along a greater length of the heater than the first portion.

The second portion of the electrically resistive heating element may have, for example, a length of between 12 mm and 20 mm. Length is determined with respect to the longitudinal dimension of the heater. The second portion of the electrically resistive heating element may have a length about 13 mm or about 14 mm.

The first portion of the electrically resistive heating element may have, for example, a length of between 8 mm and 12 mm. The first portion of the electrically resistive heating element may have a length of about 10 mm or about 11 mm.

In preferred embodiments, the second portion of the electrically resistive heating element may extend along 13.9 mm of the length of the heater, plus or minus 0.5 mm, and the first portion of the electrically resistive heating element may extend along 10.5 mm of the length of the heater, plus or minus 0.5 mm.

As used herein, the term 'aerosol-forming substrate' relates to a substrate capable of releasing volatile compounds that can form an aerosol. Such volatile compounds may be released by heating the aerosol-forming substrate. An aerosol-forming substrate may conveniently be part of an aerosol-generating article or smoking article.

As used herein, the terms 'aerosol-generating article' and 'smoking article' refer to an article comprising an aerosol-forming substrate that is capable of releasing volatile compounds that can form an aerosol. For example, an aerosol-generating article may be a smoking article that generates an aerosol that is directly inhalable into a user's lungs through the user's mouth. An aerosol-generating article may be disposable. A smoking article comprising an aerosol-forming substrate comprising tobacco is referred to as a tobacco stick.

The first portion is heated to a higher temperature than the second portion as a result of the electrical current passing through the heating element. In one embodiment, the first portion of the heating element is configured to reach a temperature of between about 300° C. and about 550° C. in use. Preferably, the heating element is configured to reach a temperature of between about 320° C. and about 350° C.

The heater mount provides structural support to the heater and allows it to be securely fixed within an aerosol-generating device. The heater mount may comprise a polymeric material and advantageously is formed from a mouldable polymeric material, such as polyether ether ketone (PEEK). The use of a mouldable polymer allows the heater mount to be moulded around the heater and thereby firmly hold the heater. It also allows the heater mount to be produced with a desired external shape and dimensions in an inexpensive manner. The heater substrate may have mechanical features, such as lugs or notches, which enhance the fixing of the heater mount to the heater. It is of course possible to use other materials for the heater mount, such as a ceramic material. Advantageously, the heater mount may be formed from a mouldable ceramic material.

Preferably, the heating mount extends along a considerable portion of the holding portion, that is the portion of the heater substrate on which the second portion of the heater element is supported. The heater substrate may be formed from a brittle material and the heater mount may provide support to prevent flexing and torsion of the heater.

The heater may need to penetrate a non-consumable element of an aerosol-generating article, such as a tube. It may be preferable that the heater mount is shaped to increase the length of heater that is in contact with the heater mount while also facilitating engagement with an aerosol-generating article having a non-consumable front element such as a tube located at a distal end of the article. Thus, at least a portion of the heater mount may step inwards or taper inwards as it extends along the holding portion in a direction towards the heating portion. The step or taper may allow a portion of the heater mount to be inserted into a tubular front element. Thus, the heater mount may provide support along most of the holding portion. Preferably, at least a portion of the heater mount extends along the holding portion for greater than 50% of the length of the holding portion, preferably greater than 60%, or greater than 70% or greater than 80%, or greater than 90%. It may be preferable that at least a portion of the heater mount is cone-shaped. Cone-shaped includes pyramid-shaped. The entire heater mount may be cone shaped, with the apex of the cone pointing towards the heating portion of the heater. Alternatively, the heater mount may comprise a cone-shaped projection that has an apex pointing towards the heating portion of the heater. A configuration in which at least a portion of the heater mount is cone-shaped may provide optimised support of the heater while still allowing engagement with an aerosol-generating article.

The use of a polymer to hold the heater means that the temperature of the heater in the vicinity of the heater mount must be controlled to be below the temperature at which the polymer will melt burn or otherwise degrade. The temperature of the heater at a portion that passes through a non-consumable element located at a distal end of an aerosol-generating article should also not exceed a temperature at which the material forming the non-consumable element degrades. It is also inefficient to heat a non-consumable component of an aerosol-generating article. At the same time the temperature of the portion of the heater within the aerosol-forming substrate must be sufficient to produce an aerosol with the desired properties. It is therefore desirable to extend the length of the second portion with respect to the first portion. It is also desirable to ensure that the second portion of the heating element remains below a maximum allowable temperature during use.

In an electrically resistive heater, the heat produced by the heater is dependent on the resistance of the heating element. For a given current, the higher the resistance of the heating element the more heat is produced. It is desirable that most of the heat produced is produced by the first portion of the heating element. Accordingly it is desirable that the first portion of the heating element has a greater electrical resistance per unit length than the second portion of the heater element.

Advantageously, the heating element may comprise portions formed from different materials. The first portion of the heating element may be formed from a first material and the second portion of the heating element may be formed from a second material, wherein the first material has a greater electrical resistivity coefficient than the second material. For example, the first material may be Ni—Cr (Nickel-Chromium), platinum, tungsten or alloy wire and the second material may be gold or silver or copper. The dimensions of the first and second portions of the heater element may also differ to provide for a lower electrical resistance per unit length in the second portion.

The materials for the first and second portions of the heating element may be selected for their thermal properties as well as their electrical properties. Advantageously, the second portion of the heating element may have a low thermal conductivity, in order to reduce conduction of heat from the heating area to the heater mount. Accordingly, the choice of material for the second portion of the heating element may be a balance between high electrical conductivity and low thermal conductivity, at least in the region between the first portion of the heating element and the heater mount. In practice, gold has been found to be a good choice of material for the second portion of the heating element. Alternatively, silver may comprise the second portion material.

Advantageously, the second portion of the heating element may comprise two sections, each of the two sections being separately connected to the first portion of the heating element to define an electrical flow path from the one section of the second portion to the first portion and then to the other section of the second portion. The heater mount may surround both sections of the second portion. It is of course possible for the second portion to comprise more than two portions, each electrically connected to the first portion.

The heating element may comprise a third portion configured for electrical connection to power supply, wherein the third portion is positioned on an opposite side of the heater mount to the first portion of the heating element. The third portion may be formed from a different material to the first and second portions, and may be chosen to provide a low electrical resistance and good connection properties, for example, easily solderable. In practice, silver has been found to be a good choice for the third portion. Alternatively, gold may be used as the material for the third portion. The third portion may comprise a plurality of sections, each connected to a section of the second portion of the heating element.

The heater substrate may be formed from an electrically insulating material and may be a ceramic material such as Zirconia or Alumina. The heater substrate may provide a mechanically stable support for the heating element over a wide range of temperatures and may provide a rigid structure suitable for insertion into an aerosol-forming substrate. The heater substrate may comprise a planar surface on which the heating element is positioned and a tapered end configured to allow for insertion into an aerosol-forming substrate. The heater substrate advantageously has a thermal conductivity of less than or equal to 2 Watts per metre Kelvin.

In one embodiment, the first portion of the heating element may be formed from material having a defined relationship between temperature and resistivity. This allows the heater to be used both to the heat the aerosol-forming substrate and to monitor temperature during use. Advantageously, the first portion has a greater temperature coefficient of resistance than the second portion. This ensures that the value of resistance of the heater element predominantly reflects the temperature of the first portion of the heater element. Platinum has been found to be a good choice for the first portion of the heater element.

Advantageously, the first portion of the heating element is spaced from the heater mount. The part of the heater between the first portion of the heating element and the heater mount advantageously has a thermal gradient between a higher temperature at the first portion of the heater element and a lower temperature at the heater mount. The distance between the first portion of the heating element and the heater mount is chosen to ensure a sufficient temperature drop is obtained. But it is also advantageous that the distance is not greater than necessary both in order to reduce the size of the heater assembly and to ensure the heater assembly is as robust as possible. The greater the length of the heater beyond the heater mount, the more prone it is to snapping or bending if dropped or during repeated insertion and withdrawal from solid aerosol-forming substrates.

Advantageously, under normal operating conditions, when the first portion of the heating element is at a temperature of between about 300 and about 550 degrees centigrade, at the points of contact with the heater mount the second portion is at a temperature of less than 200 degrees centigrade. "Normal operating conditions" in this context means at standard ambient temperature and pressure, which is a temperature of 298.15 K (25 C, 77 F) and an absolute pressure of 100 kPa (14.504 psi, 0.986 atm). Normal operating conditions includes the operation of the heater assembly when positioned within a housing of an aerosol-generating device or outside of the housing of an aerosol-generating device.

Advantageously, the heater assembly is configured such that, if the maximum temperature of the first portion is $T_1$, the ambient temperature is $T_0$, and the temperature of the second portion of the heater element in contact with the heater mount is $T_2$, then:

$$(T_1-T_0)/(T_2-T_0)>2$$

The heating assembly may comprise one or more layers of material covering the heating element. Advantageously a protective layer, formed for example from glass, may be provided over the heating element to prevent oxidation or other corrosion of the heating element. The protective layer may completely cover the heater substrate. The protective layer, or other layers, may also provide for improved thermal distribution over the heater and may make the heater easier to clean. An underlying layer of material, such as glass, may also be provided between the heating element and heater substrate in order to improve thermal distribution over the heater. The underlying layer of material may also be used to improve the process of forming the heating element.

The dimensions of the heater may be chosen to suit the application of the heating assembly, and it should be clear that the width, length and thickness of the heater may be selected independently of one another. In one embodiment the heater is substantially blade shaped and has a tapered end for insertion into an aerosol-forming substrate. The heater may have a total length of between about 15 mm and about 30 mm, and advantageously between about 20 mm and about 25 mm. The surface of the heater on which the heating element is positioned may have a width of between about 2 mm and about 10 mm, and advantageously between about 3 mm and about 6 mm. The heater may have a thickness of between about 0.2 mm and about 0.5 mm and preferably between 0.3 mm and 0.4 mm. The active heating area of the heater, corresponding to the portion of the heater in which the first portion of the heating element is positioned, may have a length of between 5 mm and 20 mm and advantageously is between 8 mm and 15 mm. The distance between the heater mount and the first portion of the heating element may be at least 2 mm and advantageously at least 2.5 mm. In a preferred embodiment the distance between the heater mount and the first portion of the heating element is 3 mm.

In an aspect of the invention, there may be provided an aerosol-generating device comprising: a housing, a heating assembly in accordance as described above, wherein the heater mount is coupled to the housing, an electrical power supply connected to the heating element, and a control element configured to control the supply of power from the power supply to the heating element. The housing may define a cavity surround the first portion of the heating element, the cavity configured to receive an aerosol-forming article containing an aerosol forming substrate.

As used herein, an 'aerosol-generating device' relates to a device that interacts with an aerosol-forming substrate to generate an aerosol. The aerosol-forming substrate may be part of an aerosol-generating article, for example part of a smoking article. An aerosol-generating device may be a smoking device that interacts with an aerosol-forming substrate of an aerosol-generating article to generate an aerosol that is directly inhalable into a user's lungs thorough the user's mouth. An aerosol-generating device may be a holder.

The heater mount may form a surface closing one end of the cavity.

The device is preferably a portable or handheld device that is comfortable to hold between the fingers of a single hand. The device may be substantially cylindrical in shape and has a length of between 70 and 120 mm. The maximum diameter of the device is preferably between 10 and 20 mm. In one embodiment the device has a polygonal cross section and has a protruding button formed on one face. In this embodiment, the diameter of the device is between 12.7 and 13.65 mm taken from a flat face to an opposing flat face; between 13.4 and 14.2 taken from an edge to an opposing edge (i.e., from the intersection of two faces on one side of the device to a corresponding intersection on the other side), and between 14.2 and 15 mm taken from a top of the button to an opposing bottom flat face.

The device may be an electrically heated smoking device.

The device may include other heaters in addition to the heater assembly according to the first aspect. For example the device may include an external heater positioned around a perimeter of the cavity. An external heater may take any suitable form. For example, an external heater may take the form of one or more flexible heating foils on a dielectric substrate, such as polyimide. The flexible heating foils can be shaped to conform to the perimeter of the cavity. Alternatively, an external heater may take the form of a metallic grid or grids, a flexible printed circuit board, a moulded interconnect device (MID), ceramic heater, flexible carbon fibre heater or may be formed using a coating technique, such as plasma vapour deposition, on a suitable shaped substrate. An external heater may also be formed using a metal having a defined relationship between temperature and resistivity. In such an exemplary device, the metal may be formed as a track between two layers of suitable insulating materials. An external heater formed in this manner may be used to both heat and monitor the temperature of the external heater during operation.

The power supply may be any suitable power supply, for example a DC voltage source such as a battery. In one embodiment, the power supply is a Lithium-ion battery. Alternatively, the power supply may be a Nickel-metal hydride battery, a Nickel cadmium battery, or a Lithium based battery, for example a Lithium-Cobalt, a Lithium-Iron-Phosphate, Lithium Titanate or a Lithium-Polymer battery.

The control element may be a simple switch. Alternatively the control element may be electric circuitry and may comprise one or more microprocessors or microcontrollers.

In a third aspect of the invention, there is provided an aerosol-generating system comprising an aerosol-generating device according to the second aspect of the invention and one or more aerosol-forming articles configured to be received in the cavity of the aerosol-generating device. The aerosol-generating article includes a non-consumable element located at a distal end of the article, upstream from an aerosol-forming substrate.

The aerosol-generating system may comprise a heated aerosol-generating article, the heated aerosol-generating article comprising a plurality of components including an aerosol-forming substrate assembled within a wrapper to form a rod having a mouth end and a distal end upstream from the mouth end. A hollow tube, which may have an external diameter of between 5 mm and 15 mm and a length of between 5 mm and 15 mm, may be disposed upstream from the aerosol-forming substrate within the wrapper. The heater of the aerosol-generating device is of sufficient length to extend through the lumen of the hollow tube and penetrate the aerosol-forming substrate when the heated aerosol-generating article is engaged with the aerosol-generating device.

The hollow tube may be rigid and may be formed from a substantially non-flammable material. As defined herein, a non-flammable material is a material that is difficult or impossible to ignite using a flame having a temperature of between 800° C. to 1700° C. and typically in the range of 800° C. to 1200° C. In general, any material that does not substantially release a toxic or otherwise harmful or undesirable compound in a temperature range between approximately 800° C. to 1200° C. or up to 1700° C. is within the substantially non-flammable materials contemplated herein.

A pierceable film may span one end of the hollow tube. The hollow tube has a proximal end and a distal end. The pierceable film may span the distal end of the hollow tube. The pierceable film may span the proximal end of the hollow tube. A hollow tube spanned by a pierceable film may protect the distal end of the rod from ignition in case a user applies a flame and draws on the mouth end of the article. The heat from the flame impinges the hollow tube, which is non-flammable. The aerosol-forming substrate, located downstream of the hollow tube is less likely to reach its combustion temperature than if it were located at the distal end of the heated aerosol-generating article. Furthermore, a pierecable film helps prevent air from being drawn through the rod. Thus, the risk of inadvertent or unintended ignition of the aerosol-forming substrate is reduced.

Preferably the hollow tube is a rigid hollow tube formed from a polymer, a metal or a ceramic. The rigid hollow tube is preferably formed from a material selected from the list consisting of metal foil, ceramic, highly filled paper, cellulose acetate and Polyaryletherketone (PAEK) polymer.

The aerosol-forming article may be a smoking article. During operation a smoking article containing the aerosol-forming substrate may be partially contained within the aerosol-generating device.

The smoking article may be substantially cylindrical in shape. The smoking article may be substantially elongate. The smoking article may have a length and a circumference substantially perpendicular to the length. The aerosol-forming substrate may be substantially cylindrical in shape. The aerosol-forming substrate may be substantially elongate. The aerosol-forming substrate may also have a length and a circumference substantially perpendicular to the length.

The smoking article may have a total length between approximately 30 mm and approximately 100 mm. The smoking article may have an external diameter between approximately 5 mm and approximately 12 mm. The smoking article may comprise a filter plug. The filter plug may be located at a downstream end of the smoking article. The filter plug may be a cellulose acetate filter plug. The filter plug is approximately 7 mm in length in one embodiment, but may have a length of between approximately 5 mm to approximately 10 mm.

In one embodiment, the smoking article has a total length of approximately 45 mm. The smoking article may have an external diameter of approximately 7.2 mm. Further, the aerosol-forming substrate may have a length of approximately 10 mm. Alternatively, the aerosol-forming substrate may have a length of approximately 12 mm. Further, the diameter of the aerosol-forming substrate may be between approximately 5 mm and approximately 12 mm. The smoking article may comprise an outer paper wrapper. Further, the smoking article may comprise a separation between the aerosol-forming substrate and the filter plug. The separation may be approximately 18 mm, but may be in the range of approximately 5 mm to approximately 25 mm.

The aerosol-forming substrate may be a solid aerosol-forming substrate. Alternatively, the aerosol-forming substrate may comprise both solid and liquid components. The aerosol-forming substrate may comprise a tobacco-containing material containing volatile tobacco flavour compounds which are released from the substrate upon heating. Alternatively, the aerosol-forming substrate may comprise a non-tobacco material. The aerosol-forming substrate may further comprise an aerosol former that facilitates the formation of a dense and stable aerosol. Examples of suitable aerosol formers are glycerine and propylene glycol.

If the aerosol-forming substrate is a solid aerosol-forming substrate, the solid aerosol-forming substrate may comprise, for example, one or more of: powder, granules, pellets, shreds, spaghettis, strips or sheets containing one or more of: herb leaf, tobacco leaf, fragments of tobacco ribs, reconstituted tobacco, homogenised tobacco, extruded tobacco, cast leaf tobacco and expanded tobacco. The solid aerosol-forming substrate may be in loose form, or may be provided in a suitable container or cartridge. Optionally, the solid aerosol-forming substrate may contain additional tobacco or non-tobacco volatile flavour compounds, to be released upon heating of the substrate. The solid aerosol-forming substrate may also contain capsules that, for example, include the additional tobacco or non-tobacco volatile flavour compounds and such capsules may melt during heating of the solid aerosol-forming substrate.

As used herein, homogenised tobacco refers to material formed by agglomerating particulate tobacco. Homogenised tobacco may be in the form of a sheet. Homogenised tobacco material may have an aerosol-former content of greater than 5% on a dry weight basis. Homogenised tobacco material may alternatively have an aerosol former content of between 5% and 30% by weight on a dry weight basis. Sheets of homogenised tobacco material may be formed by agglomerating particulate tobacco obtained by grinding or otherwise combining one or both of tobacco leaf lamina and tobacco leaf stems. Alternatively, or in addition, sheets of homogenised tobacco material may comprise one or more of tobacco dust, tobacco fines and other particulate tobacco by-products formed during, for example, the treating, handling and shipping of tobacco. Sheets of homogenised tobacco material may comprise one or more intrinsic binders, that is tobacco endogenous binders, one or more extrinsic binders, that is tobacco exogenous binders, or a combination thereof to help agglomerate the particulate tobacco; alternatively, or in addition, sheets of homogenised tobacco material may comprise other additives including, but not limited to, tobacco and non-tobacco fibres, aerosol-formers, humectants, plasticisers, flavourants, fillers, aqueous and non-aqueous solvents and combinations thereof.

Optionally, the solid aerosol-forming substrate may be provided on or embedded in a thermally stable carrier. The carrier may take the form of powder, granules, pellets, shreds, spaghettis, strips or sheets. Alternatively, the carrier may be a tubular carrier having a thin layer of the solid substrate deposited on its inner surface, or on its outer surface, or on both its inner and outer surfaces. Such a tubular carrier may be formed of, for example, a paper, or paper like material, a non-woven carbon fibre mat, a low mass open mesh metallic screen, or a perforated metallic foil or any other thermally stable polymer matrix.

In a particularly preferred embodiment, the aerosol-forming substrate comprises a gathered crimped sheet of homogenised tobacco material. As used herein, the term 'crimped sheet' denotes a sheet having a plurality of substantially parallel ridges or corrugations. Preferably, when the aerosol-generating article has been assembled, the substantially parallel ridges or corrugations extend along or parallel to the longitudinal axis of the aerosol-generating article. This advantageously facilitates gathering of the crimped sheet of homogenised tobacco material to form the aerosol-forming substrate. However, it will be appreciated that crimped sheets of homogenised tobacco material for inclusion in the aerosol-generating article may alternatively or in addition have a plurality of substantially parallel ridges or corrugations that are disposed at an acute or obtuse angle to the longitudinal axis of the aerosol-generating article when the aerosol-generating article has been assembled. In certain embodiments, the aerosol-forming substrate may comprise a gathered sheet of homogenised tobacco material that is substantially evenly textured over substantially its entire surface. For example, the aerosol-forming substrate may comprise a gathered crimped sheet of homogenised tobacco material comprising a plurality of substantially parallel ridges or corrugations that are substantially evenly spaced-apart across the width of the sheet.

The solid aerosol-forming substrate may be deposited on the surface of the carrier in the form of, for example, a sheet, foam, gel or slurry. The solid aerosol-forming substrate may be deposited on the entire surface of the carrier, or alternatively, may be deposited in a pattern in order to provide a non-uniform flavour delivery during use.

The aerosol-generating system is a combination of an aerosol-generating device and one or more aerosol-generating articles for use with the device. However, aerosol-generating system may include additional components, such as for example a charging unit for recharging an on-board electric power supply in an electrically operated or electric aerosol-generating device Although the disclosure has been described by reference to different aspects, it should be clear that features described in relation to one aspect of the disclosure may be applied to the other aspects of the disclosure. In particular, aspects of the heater, assembly, device system or method in accordance with one aspect of the invention may be applied to any other aspect of the invention. Furthermore, although the disclosure has been by reference to smoking devices, it should be clear that medical inhaler type devices may use the features, apparatuses, and functionalities described herein.

Embodiments of the invention will now be described in detail, by way of example only, with reference to the accompanying drawings, in which.

Figure 1:
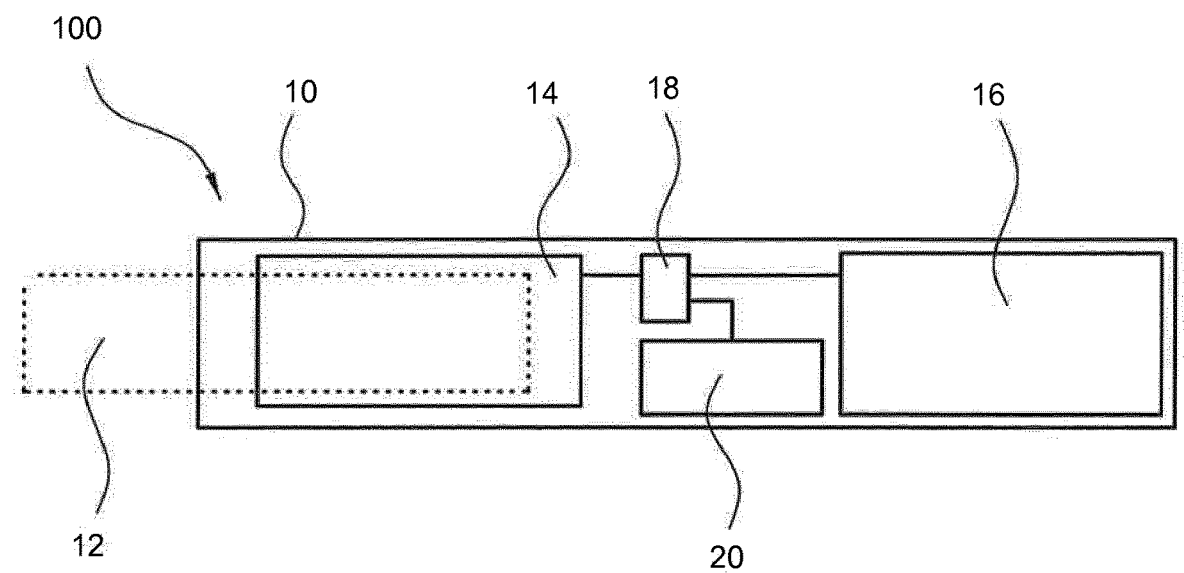
FIG. 1 is a schematic diagram of an aerosol generating device.

In FIG. 1, the components of an embodiment of an electrically heated aerosol-generating system 100 are shown in a simplified manner. Particularly, the elements of the electrically heated aerosol-generating system 100 are not drawn to scale in FIG. 1. Elements that are not relevant for the understanding of this embodiment have been omitted to simplify FIG. 1.

The electrically heated aerosol generating system 100 comprises an aerosol-generating device having a housing 10 and an aerosol-forming article 12, for example a tobacco stick. The aerosol-forming article 12 includes an aerosol-forming substrate that is pushed inside the housing 10 to come into thermal proximity with a heater 14. The aerosol-forming substrate will release a range of volatile compounds at different temperatures. By controlling the maximum operation temperature of the electrically heated aerosol generating system 100 the release of undesirable volatile compounds may be controlled.

Within the housing 10 there is an electrical energy supply 16, for example a rechargeable lithium ion battery. A controller 18 is connected to the heater 14, the electrical energy supply 16, and a user interface 20, for example a button or display. The controller 18 controls the power supplied to the heater 14 in order to regulate its temperature. Typically the aerosol-forming substrate is heated to a temperature of between 250 and 450 degrees centigrade.

Figure 2:
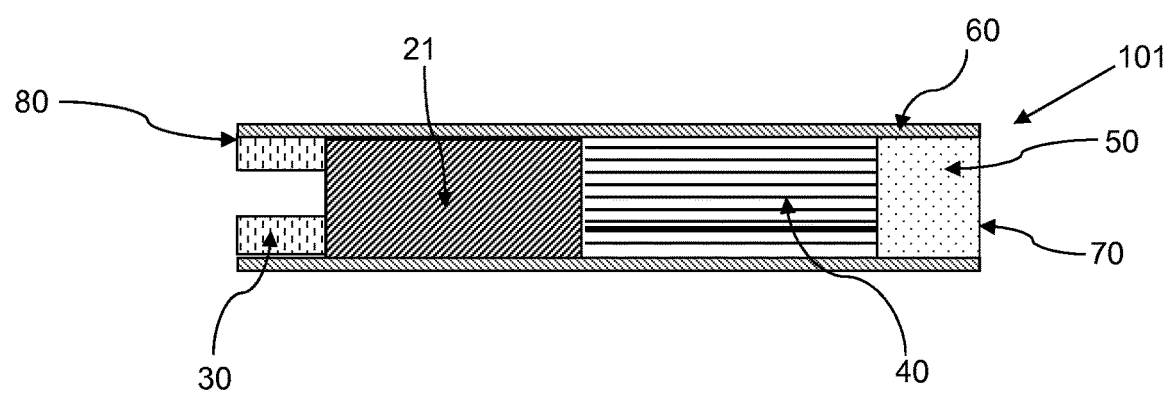
FIG. 2 is a schematic cross-sectional diagram of an embodiment of a heated aerosol-generating article for use with an aerosol generating-device.

FIG. 2 illustrates a heated aerosol-generating article 101 according to a preferred embodiment. The aerosol-generating article 101 comprises four elements arranged in coaxial alignment: a rigid hollow tube 30, an aerosol-forming substrate 21, an aerosol-cooling element 40, and a mouthpiece 50. These four elements are arranged sequentially and are circumscribed by an outer wrapper 60 to form the heated aerosol-generating article 101. The aerosol-generating article 101 has a proximal or mouth end 70, which a user inserts into his or her mouth during use, and a distal end 80 located at the opposite end of the aerosol-generating article 101 to the mouth end 70.

The distal end 80 of the aerosol-generating article may also be described as the upstream end of the aerosol-generating article 101 and the mouth end 70 of the aerosol-generating article 101 may also be described as the downstream end of the aerosol-generating article 101. Elements of the aerosol-generating article 101 located between the mouth end 70 and the distal end 80 can be described as being upstream of the mouth end 70 or, alternatively, downstream of the distal end 80.

The rigid hollow tube 30 is located at the extreme distal or upstream end of the aerosol-generating article 101. In the article shown in FIG. 2, the rigid hollow tube 30 is a hollow ceramic tube. This rigid hollow tube 30 may protect the aerosol-forming substrate from flames applied to the distal end of the article 101, thereby providing a means of reducing the chance of inadvertent ignition.

In the article illustrated in FIG. 2, the aerosol-forming substrate 21 comprises a gathered sheet of crimped homogenised tobacco material circumscribed by a wrapper. The crimped sheet of homogenised tobacco material comprises comprising glycerine as an aerosol-former.

The aerosol-cooling element 40 is located immediately downstream of the support element 30 and abuts the support element 30. In use, volatile substances released from the aerosol-forming substrate 21 pass along the aerosol-cooling element 40 towards the mouth end 70 of the aerosol-generating article 101. The volatile substances may cool within the aerosol-cooling element 40 to form an aerosol that is inhaled by the user. In the article illustrated in FIG. 2, the aerosol-cooling element comprises a crimped and gathered sheet of polylactic acid circumscribed by a wrapper 90. The crimped and gathered sheet of polylactic acid defines a plurality of longitudinal channels that extend along the length of the aerosol-cooling element 40.

The mouthpiece 50 is located immediately downstream of the aerosol-cooling element 40 and abuts the aerosol-cooling element 40. In the article illustrated in FIG. 2, the mouthpiece 50 comprises a conventional cellulose acetate tow filter of low filtration efficiency.

To assemble the aerosol-generating article 101, the four elements described above are aligned and tightly wrapped within the outer wrapper 60. In some embodiments, a distal end portion of the outer wrapper 60 of the aerosol-generating article 101 may be circumscribed by a band of tipping paper.

The aerosol-generating article 101 illustrated in FIG. 2 is designed to engage with an aerosol-generating device comprising a heating element in order to be smoked or consumed by a user. In use, the heating element of the aerosol-generating device heats the aerosol-forming substrate 21 of the aerosol-generating article 101 to a sufficient temperature to form an aerosol, which is drawn downstream through the aerosol-generating article 101 and inhaled by the user.

Figure 3:
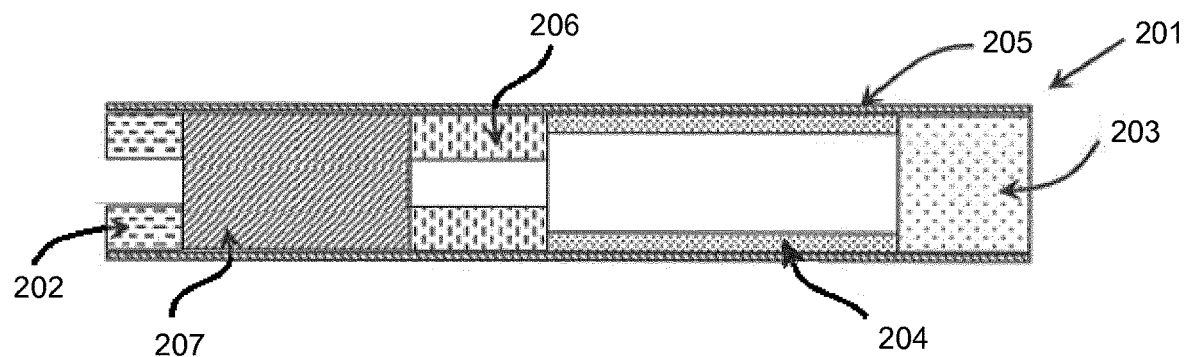
FIG. 3 is a schematic cross-sectional diagram of a further embodiment of a heated aerosol-generating article for use with an aerosol generating-device.

FIG. 3 illustrates a further embodiment of a suitable aerosol-generating article 201. The article 201 comprises five elements, a rigid hollow tube 202, an aerosol-forming substrate 207, a hollow cellulose acetate tube 206, a transfer section 204, and a mouthpiece filter 203. These five elements are arranged sequentially and in coaxial alignment and are assembled by a cigarette paper 205 to form a rod. When assembled, the article 201 is 52 millimetres long and has a diameter of 7.2 millimetres.

The rigid hollow tube 202 is a ceramic tube having a length of 7 millimetres.

The aerosol-forming substrate 207 is located downstream of the rigid hollow tube 202 and comprises a bundle of crimped cast-leaf tobacco wrapped in a filter paper. The cast-leaf tobacco includes additives, including glycerine as an aerosol-forming additive.

The cellulose acetate tube 206 is located immediately downstream of the aerosol-forming substrate 207 and is formed from cellulose acetate. The tube 206 defines an aperture having a diameter of 3.3 millimetres. One function of the tube 206 is to locate the aerosol-forming substrate 207 towards the distal end 230 of the article 201 so that it can be contacted with a heating element. The tube 206 acts to prevent the aerosol-forming substrate 207 from being forced along the article 201 towards the mouth-end 220 when a heating element is inserted.

The transfer section 204 comprises a thin-walled tube of 18 millimetres in length. The transfer section 204 allows volatile substances released from the aerosol-forming substrate 207 to pass along the article 201 towards the mouth end 20. The volatile substances may cool within the transfer section 204 to form an aerosol. An aerosol-cooling element, such as a crimped and gathered sheet of polylactic acid may be used instead of the transfer section.

The mouthpiece filter 203 is a conventional mouthpiece filter formed from cellulose acetate, tow and having a length of 7 millimetres.

The five elements identified above are assembled by being tightly wrapped within a cigarette paper 205.

Figure 4:
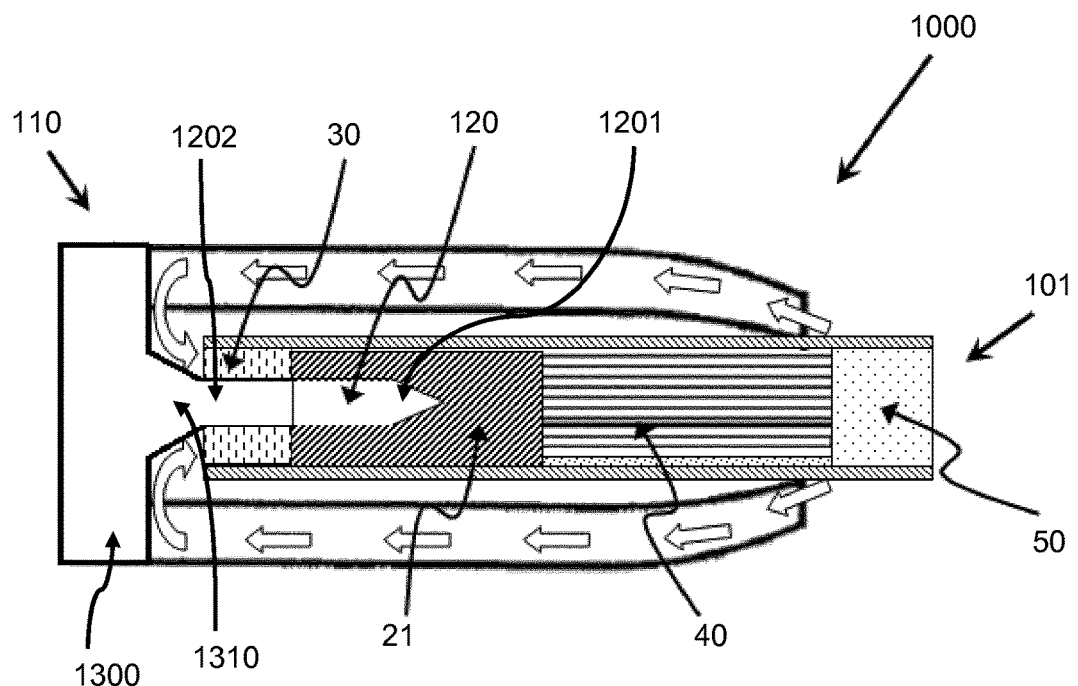
FIG. 4 is a schematic cross-section of a front end of an aerosol-generating device of the type shown in FIG. 1, with the heater inserted into an aerosol-generating article.

FIG. 4 illustrates a portion of an aerosol-generating system 1000 comprising an aerosol-generating device 110 and an aerosol-generating article 101 according to the embodiment of an article described above and illustrated in FIG. 2. The system may alternatively comprise aerosol-generating articles as described in relation to FIG. 3 above, or any other suitable aerosol-generating articles.

The aerosol-generating device 110 comprises a heating element 120. As shown in FIG. 4, the heating element 120 is mounted within an aerosol-generating article receiving chamber of the aerosol-generating device 110. In use, the user inserts the aerosol-generating article 101 into the aerosol-generating article receiving chamber of the aerosol-generating device 110 such that the heating element 120 pierces and is directly inserted into the aerosol-forming substrate 21 of the aerosol-generating article 101 through the lumen of the rigid hollow tube 30 as shown in FIG. 4. In the embodiment shown in FIG. 4, the heating element 120 of the aerosol-generating device 110 is a heater blade. The heating element 120 has a heating portion 1201 and a holding portion 1202. The holding portion 1202 extends along a greater length of the heating element 120 than the heating portion 1201. In use, the heating portion 1201 is inserted into the aerosol-forming substrate 21 of the aerosol-generating article 101. A PEEK heater mount 1300 is moulded onto the holding portion 1202 of the heating element 120. A cone-shaped projection 1310 extends from a surface of the heater mount and extends along the holding portion of the heating element 120 to increase the proportion of the heating element 120 that is supported by the heater mount.

The aerosol-generating device 110 comprises a power supply and electronics that allow the heating element 120 to be actuated. Such actuation may be manually operated or may occur automatically in response to a user drawing on an aerosol-generating article 101 inserted into the aerosol-generating article receiving chamber of the aerosol-generating device 110. A plurality of openings is provided in the aerosol-generating device to allow air to flow to the aerosol-generating article 101; the direction of air flow is illustrated by arrows in FIG. 4.

Once the internal heating element 120 is inserted into the aerosol-forming substrate 21 of the aerosol-generating article 101 and actuated, the aerosol-forming substrate 21 is heated to a temperature of approximately 375 degrees Celsius by the heating element 120 of the aerosol-generating device 110. At this temperature, volatile compounds are evolved from the aerosol-forming substrate 21 of the aerosol-generating article 101. As a user draws on the mouth end 70 of the aerosol-generating article 10, the volatile compounds evolved from the aerosol-forming substrate 21 are drawn downstream through the aerosol-generating article 101 and condense to form an aerosol that is drawn through the mouthpiece 50 of the aerosol-generating article 101 into the user's mouth.

As the aerosol passes downstream thorough the aerosol-cooling element 40, the temperature of the aerosol is reduced due to transfer of thermal energy from the aerosol to the aerosol-cooling element 40. When the aerosol enters the aerosol-cooling element 40, its temperature is approximately 60 degrees Celsius. Due to cooling within the aerosol-cooling element 40, the temperature of the aerosol as it exits the aerosol-cooling element is approximately 40 degrees Celsius.

Figure 5:
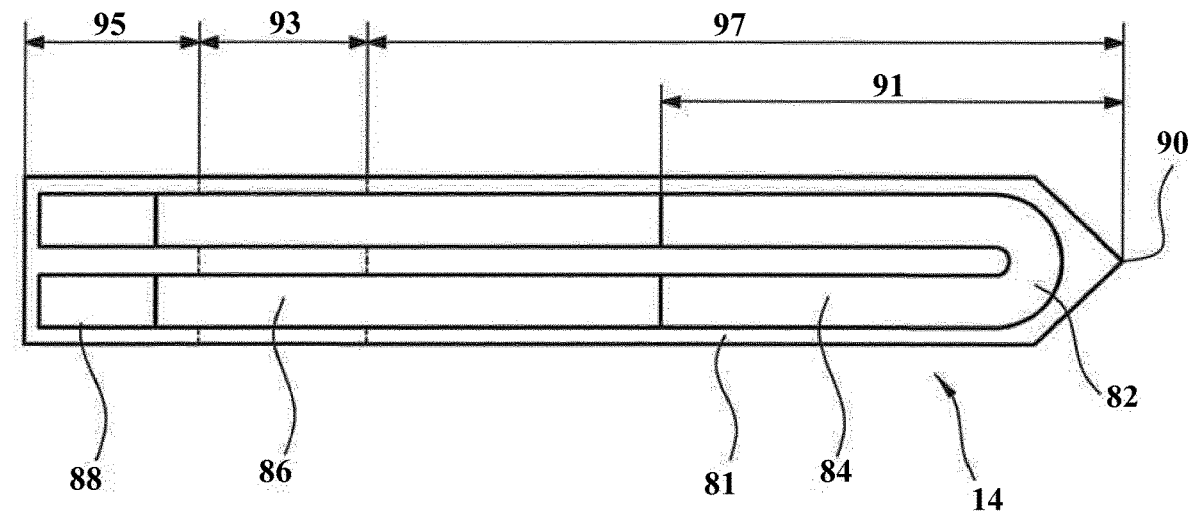
FIG. 5 is a schematic illustration of a heater in accordance with the present invention.

FIG. 5 illustrates a heater element 14 of the type shown in FIG. 4 in greater detail. The heater 14 comprises an electrically insulating heater substrate 81, which defines the shape of the heating element 14. The heater substrate 81 is formed from an electrically insulating material, which may be, for example, alumina ($Al_2O_3$) or stabilized zirconia ($ZrO_2$). It will be apparent to one of ordinary skill in the art that the electrically insulating material may be any suitable electrically insulating material and that many ceramic materials are suitable for use as the electrically insulating substrate. The heater substrate 81 is substantially blade-shaped. That is, the heater substrate has a length that in use extends along the longitudinal axis of an aerosol-forming article engaged with the heater, a width and a thickness. The width is greater than the thickness. The heater substrate 81 terminates in a point or spike 90 for penetrating an aerosol-forming substrate 30.

Figure 6:
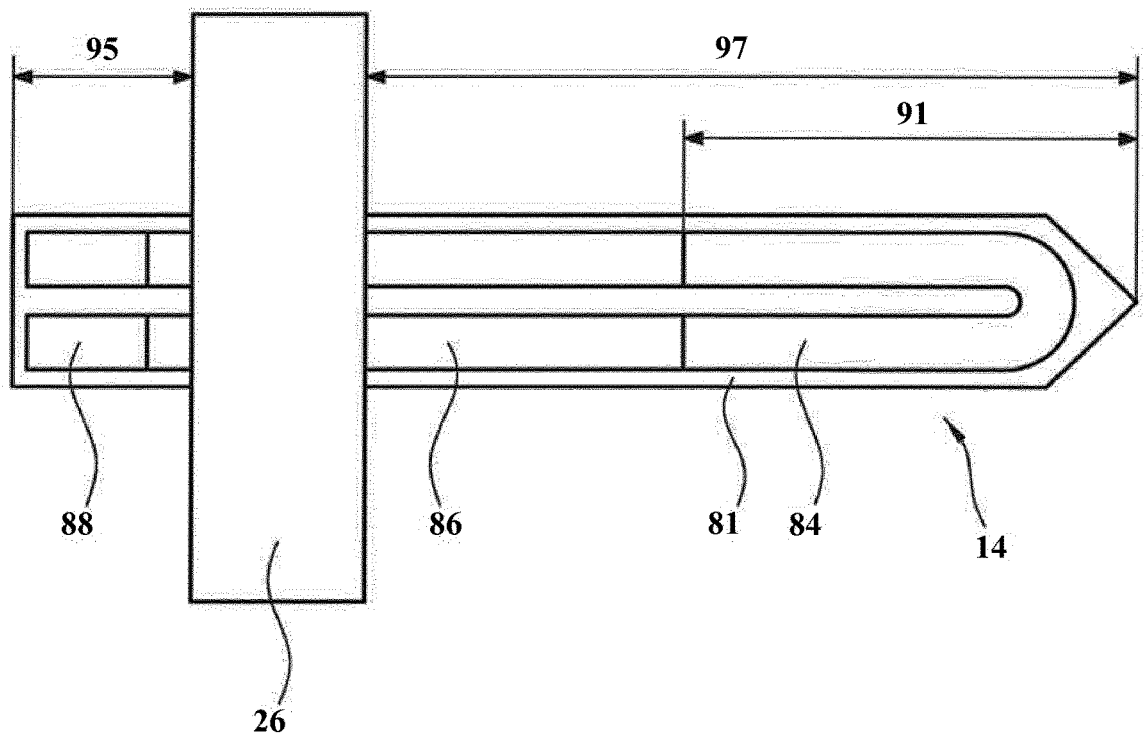
FIG. 6 shows the heater of FIG. 5 with a heater mount assembled to it.

A heating element 82 formed from electrically conductive material is deposited on a planar surface of the heater substrate 80 using evaporation or any other suitable technique. The heating element is formed in three distinct portions. A first portion 84 is formed from platinum. The first portion is positioned in the active heating area or heating portion 91. This is the area of the heater which reaches the maximum temperature and provides heat to an aerosol-forming substrate in use. The first portion is U-shaped or in the shape of a hairpin. A second portion 86 is formed from gold. The second portion comprises two parallel tracks, each connected to an end of the first portion 84. The second portion is located in a holding portion, which spans the holding area 93 of the heater. The holding area is the area of the heater that is in contact with the heater mount 26, as shown in FIG. 6. A third portion 88 is formed from silver. The third portion is positioned in the connecting area 95 and provides bonding pads to which external wires can be fixed using solder paste or other bonding techniques. The third portion comprises two parallel pads, each connected to an end of one of the parallel tracks of the second portion 86, opposite to the first portion 84. The third portion 88 is positioned on an opposite side of the holding area 93 to the first portion.

The shape, thickness and width of the first, second and third portions may be chosen to provide the desired resistance and temperature distribution in use. However, the first portion has a significantly greater electrical resistance per unit length than the second and third portions and, as a result, when an electrical current passes through the heating element 82, it is the first portion that generates the most heat and so reaches the highest temperature. The second and third portions are configured to have a very low electrical resistance and so provide very little Joule heating. The total electrical resistance of the heating element is about 0.80 Ohms at 0° C., rising to about 2 Ohms when the active heating area 91 reaches 400° C. The battery voltage of the lithium ion battery is around 3.7 Volts so that the typical peak current supplied by the power supply (at 0° C.) is around 4.6 A.

The first portion 84 has a length of 10.5 mm. The second portion 86 has a length of 13.9 mm.

Platinum has a positive temperature coefficient of resistance and so the electrical resistance of the first portion 84 increases with increasing temperature. Gold and silver have lower temperature coefficients of resistance, and the second and third portions will not experience as great a temperature rise as the first portion. This means that changes in resistance of the second and third portions will be small compared to changes in the resistance of the first portion. As a result, the resistance of the heating element 82 can be used to provide a measure of the temperature of the first portion 84 of the heating element, which is the temperature of the portion of the heater in contact with the aerosol-forming substrate. An arrangement for using a resistive element as both a heater and a temperature sensor is described in EP2110033 B1.

FIG. 6 shows the heater 14 assembled to a heater mount 26 to form a heating assembly. The heater mount 26 is formed from polyether ether ketone (PEEK) and is injection moulded around the heater to surround the holding area 93. The heater substrate 81 may be formed with notches or protrusion in the holding area to ensure a strong fixing between the heater mount and the heater. In this embodiment the heater mount 26 has a circular cross-section to engage a circular housing of the aerosol-generating device. However, the heater mount may be moulded to have any desired shape and any desired engagement features for engaging with other components of the aerosol-generating device.

Figure 7:
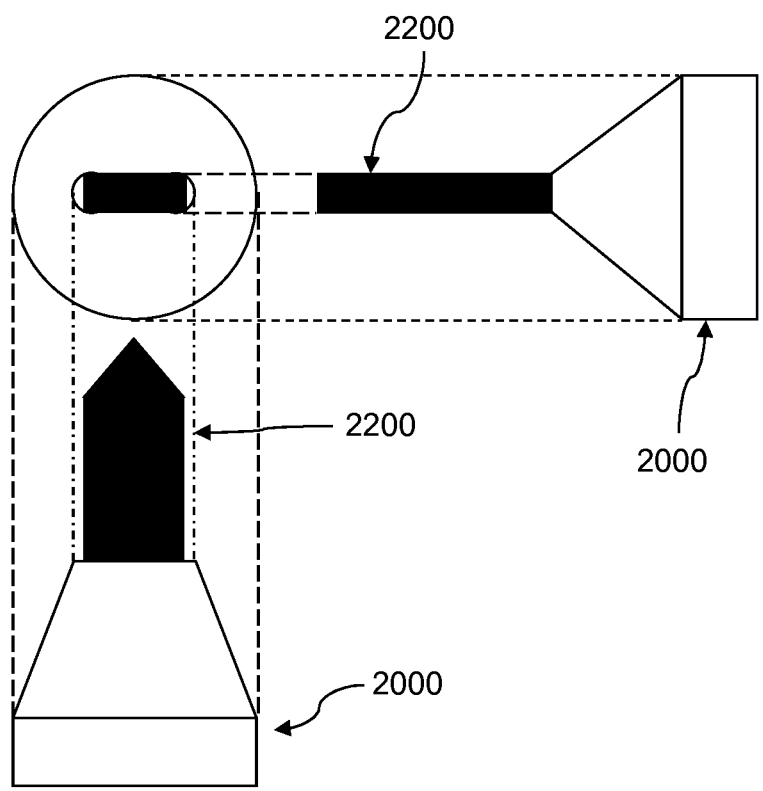
FIG. 7 illustrates an embodiment of a heater assembly including a cone-shaped heater mount.

FIG. 7 illustrates an optional shape for a heater mount 2000. The heater mount 2000 is moulded to the holding portion of a heater 2200. The heater mount is circular in cross-section and includes a portion having parallel sides for engagement with the housing of an aerosol generating device. The heater mount also includes a tapered portion forming a cone with an apex towards the tip of the heater. The cone-shape of this portion of the heater mount allows additional support to the heater. In preferred embodiments the heater support is in contact with at least 9 or 10 mm length of the heater.

The exemplary embodiments described above illustrate but are not limiting. In view of the above discussed exemplary embodiments, other embodiments consistent with the above exemplary embodiments will now be apparent to one of ordinary skill in the art.

The invention claimed is:

1. A heating assembly for heating an aerosol-forming substrate, comprising:
   a heater comprising an electrically resistive heating element and a heater substrate; and
   a heater mount coupled to the heater,
   wherein the electrically resistive heating element comprises a first portion and a second portion configured such that, when an electrical current is passed through the heating element, the first portion is heated to a higher temperature than that of the second portion,
   wherein the first portion of the electrically resistive heating element is disposed on a heating area of the heater substrate and the second portion of the electrically resistive heating element is disposed on a holding area of the heater substrate,
   wherein the heater mount is fixed to the holding area of the heater substrate,
   wherein the second portion of the electrically resistive heating element is longer than the first portion of the electrically resistive heating element, and
   wherein the second portion of the electrically resistive heating element has a length of between 12 mm and 20 mm.

2. The heating assembly according to claim 1, wherein the first portion of the electrically resistive heating element has a length of between 8 mm and 12 mm.

3. The heating assembly according to claim 1,
wherein the second portion of the electrically resistive heating element extends along 13.9 mm of a length of the heater plus or minus 0.5 mm, and
wherein the first portion of the electrically resistive heating element extends along 10.5 mm of the length of the heater plus or minus 0.5 mm.

4. The heating assembly according to claim 1, wherein the heater mount comprises a moldable polymeric material.

5. The heating assembly according to claim 1,
wherein the first portion of the electrically resistive heating element is formed from a first material and the second portion of the electrically resistive heating element is formed from a second material, and
wherein the first material has a greater electrical resistivity coefficient than that of the second material.

6. The heating assembly according to claim 1,
wherein the electrically resistive heating element further comprises a third portion configured for electrical connection to a power supply, and
wherein the third portion is disposed on an opposite side of the heater mount to the first portion of the electrically resistive heating element.

7. The heating assembly according to claim 1, wherein at least a portion of the heater mount extends along the holding area and tapers inward in a direction towards the heating portion.

8. The heating assembly according to claim 1, wherein at least a portion of the heater mount extends along the holding area for greater than 50% of a length of the holding area.

9. The heating assembly according to claim 1, wherein at least a portion of the heater mount is cone-shaped.

10. An aerosol-generating device, comprising:
a housing;
a heating assembly, comprising:
a heater comprising an electrically resistive heating element and a heater substrate, and
a heater mount coupled to the housing,
wherein the electrically resistive heating element comprises a first portion and a second portion configured such that, when an electrical current is passed through the heating element, the first portion is heated to a higher temperature than that of the second portion,
wherein the first portion of the electrically resistive heating element is disposed on a heating area of the heater substrate and the second portion of the electrically resistive heating element is disposed on a holding area of the heater substrate,
wherein the heater mount is fixed to the holding area of the heater substrate,
wherein the second portion of the electrically resistive heating element is longer than the first portion of the electrically resistive heating element, and
wherein the second portion of the electrically resistive heating element has a length of between 12 mm and 20 mm;
an electrical power supply connected to the electrically resistive heating element; and
a control element configured to control a supply of power from the electrical power supply to the electrically resistive heating element.

11. The aerosol-generating device according to claim 10, wherein the housing defines a cavity surrounding the first portion of the electrically resistive heating element, the cavity being configured to receive an aerosol-forming article containing an aerosol-forming substrate.

12. An aerosol-generating system, comprising:
an aerosol-generating device, comprising:
a housing;
a heating assembly, comprising:
a heater comprising an electrically resistive heating element and a heater substrate, and
a heater mount coupled to the housing,
wherein the electrically resistive heating element comprises a first portion and a second portion configured such that, when an electrical current is passed through the heating element, the first portion is heated to a higher temperature than that of the second portion,
wherein the first portion of the electrically resistive heating element is disposed on a heating area of the heater substrate and the second portion of the electrically resistive heating element is disposed on a holding area of the heater substrate,
wherein the heater mount is fixed to the holding area of the heater substrate,
wherein the second portion of the electrically resistive heating element is longer than the first portion of the electrically resistive heating element, and
wherein the second portion of the electrically resistive heating element has a length of between 12 mm and 20 mm;
an electrical power supply connected to the electrically resistive heating element; and
a control element configured to control a supply of power from the electrical power supply to the electrically resistive heating element; and
a heated aerosol-generating article comprising a plurality of components including an aerosol-forming substrate assembled within a wrapper forming a rod having a mouth end and a distal end upstream from the mouth end, wherein a hollow tube having an external diameter of between 5 mm and 15 mm and a length of between 5 mm and 15 mm is disposed upstream from the aerosol-forming substrate within the wrapper, the heater of the aerosol-generating device extending through the hollow tube and penetrating the aerosol-forming substrate when the heated aerosol-generating article is engaged with the aerosol-generating device.

13. The aerosol-generating system according to claim 12, wherein the aerosol-generating article further comprises an aerosol-cooling element and a mouthpiece filter disposed downstream of the aerosol-forming substrate.

* * * * *